(12) United States Patent
White et al.

(10) Patent No.: US 7,790,932 B1
(45) Date of Patent: Sep. 7, 2010

(54) HYDROFORMYLATION PROCESS

(75) Inventors: Daniel F. White, West Chester, PA (US); Ine Boogaerts, Dundee (GB); David John Cole-Hamilton, Fife (GB)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 12/653,878

(22) Filed: Dec. 21, 2009

(51) Int. Cl.
*C07C 45/50* (2006.01)
*B01J 31/00* (2006.01)

(52) U.S. Cl. .................. 568/454; 502/152; 502/155

(58) Field of Classification Search .............. 568/454; 502/152, 155
See application file for complete search history.

(56) References Cited

U.S. PATENT DOCUMENTS

| 4,064,145 | A | 12/1977 | Taylor |
| 4,215,077 | A | 7/1980 | Matsumoto et al. |
| 4,238,419 | A | 12/1980 | Matsumoto et al. |
| 4,306,087 | A | 12/1981 | Matsumoto et al. |
| 4,567,305 | A | 1/1986 | Matsumoto et al. |
| 4,678,857 | A | 7/1987 | Dureanleau et al. |
| 5,290,743 | A | 3/1994 | Chang |
| 6,127,584 | A | 10/2000 | Zajacek et al. |
| 6,225,509 | B1 | 5/2001 | Dubner et al. |
| 7,271,295 | B1 | 9/2007 | White et al. |
| 7,279,606 | B1 | 10/2007 | White |

FOREIGN PATENT DOCUMENTS

| JP | 06-279344 | 10/1994 |
| JP | 06-279345 | 10/1994 |

OTHER PUBLICATIONS

Breit et al., "Self-Assembly of Bidentate Ligands for Combinatorial Homogeneous Catalysis Based on an A-T Base-Pair Model," *Angew. Chem. Int. Ed.*, 44 (2005) 1640-1643.
Weis et al., "Self-Assembly of Bidentate Ligands for Combinatorial Homogeneous Catalysis: Asymmetric Rhodium-Catalyzed Hydrogenation," *Journal of American Chemical Society*, 128, (2006), p. 4188-4189.

*Primary Examiner*—Sikarl A Witherspoon
(74) *Attorney, Agent, or Firm*—Kevin M. Carroll

(57) ABSTRACT

A catalyst, useful for the hydroformylation of allyl alcohol, is described. The catalyst comprises a rhodium complex and a 6-bis(3,5-dialkylphenyl)phosphino-N-pivaloyl-2-aminopyridine or a 3-bis(3,5-dialkylphenyl)phosphino-2H-isoquinolin-1-one. The invention also includes a process for the production of 4-hydroxybutyraldehyde comprising reacting allyl alcohol with a mixture of carbon monoxide and hydrogen in the presence of a solvent and the catalyst. The process gives a high ratio of the linear product 4-hydroxybutyraldehyde to the branched co-product 3-hydroxy-2-methylpropionaldehyde.

14 Claims, No Drawings

HYDROFORMYLATION PROCESS

FIELD OF THE INVENTION

This invention relates to a process for hydroformylating allyl alcohol to produce 4-hydroxybutyraldehyde.

BACKGROUND OF THE INVENTION

The hydroformylation of allyl alcohol is a well known and commercially practiced process. See, for example, U.S. Pat. Nos. 4,064,145, 4,215,077, 4,238,419, 4,678,857, and 5,290,743. In the hydroformylation reaction, allyl alcohol is reacted with a $CO/H_2$ gas mixture in the presence of a catalyst to form 4-hydroxybutyraldehyde (HBA). The HBA may then be separated from the catalyst, e.g., by water extraction, and hydrogenated to form 1,4-butanediol (BDO). See U.S. Pat. No. 5,504,261.

Various catalyst systems have been employed for the allyl alcohol hydroformylation reaction, most notably a rhodium complex together with a phosphine ligand (see, e.g., U.S. Pat. Nos. 4,064,145, 4,238,419, and 4,567,305). Commonly employed phosphine ligands are trisubstituted phosphines such as triphenyl phosphine. Breit et al., in *Angew. Chem. Int. Ed.*, 2005, 44, 1640 and *J. Am. Chem. Soc.*, 2006, 128, 4128, teach the self-assembly of bidentate ligands by combination of the phosphines of 2-aminopyridines and isoquinolones, and their use in asymmetric hydrogenation and the hydroformylation of 1-octene.

One disadvantage of the allyl alcohol hydroformylation process is that other co-products or byproducts are also formed in addition to the desired HBA linear product. The hydroformylation of allyl alcohol typically produces some 3-hydroxy-2-methylpropionaldehyde (HMPA) branched co-product and $C_3$ byproducts such as n-propanol and propionaldehyde. Although HMPA may be hydrogenated to produce 2-methyl-1,3-propanediol (MPD), which is a useful material, the MPD co-product reduces the yield of BDO. Formation of the $C_3$ byproducts effectively represents another yield loss in the process which can have a severe adverse effect on the process economics.

To increase BDO yields, research continues to improve the hydroformylation process and reduce less desired co-product/byproducts. U.S. Pat. No. 6,127,584 discloses that the use of a trialkyl phosphine ligand having at least 2 methyl groups results in increased HBA:HMPA ratio. The use of diphosphine ligands has also been found to improve the HBA:HMPA ratio. The hydroformylation of allyl alcohol using rhodium complex catalysts and diphosphine ligands such as DIOP, XANTPHOS, or trans-1,2-bis(diphenylphosphinomethyl)cyclobutane is shown in the art, notably in Japan Kokai Nos. 06-279345 and 06-279344 and U.S. Pat. No. 4,306,087. U.S. Pat. No. 6,225,509 discloses that maintaining the concentration of CO in the reaction liquid above about 4.5 mmols/liter reduces the make of undesirable $C_3$ co-products when using a catalyst comprised of a rhodium complex and a ligand such as DIOP. In addition, U.S. Pat. Nos. 7,271,295 and 7,279,606 disclose the use of a 2,3-O-isopropylidene-2,3-dihydroxy-1,4-bis[bis(3,5-di-n-alkylphenyl)phosphino]butane ligand or a trans-1,2-bis[bis(3,5-di-n-alkylphenyl)phosphinomethyl]cyclobutane ligand, respectively.

In sum, new processes for hydroformylating allyl alcohol to produce 4-hydroxybutyraldehyde are needed. Particularly valuable processes would result in high ratios of 4-hydroxybutyraldehyde to 3-hydroxy-2-methylpropionaldehyde.

SUMMARY OF THE INVENTION

The invention is a process that comprises reacting allyl alcohol with carbon monoxide and hydrogen in the presence of a solvent and a catalyst to produce 4-hydroxybutyraldehyde. The catalyst comprises a rhodium complex and a 6-bis(3,5-dialkylphenyl)phosphino-N-pivaloyl-2-aminopyridine or a 3-bis(3,5-dialkylphenyl)phosphino-2H-isoquinolin-1-one. The invention also includes the catalyst. The invention gives a surprisingly high ratio of 4-hydroxybutyraldehyde compared to 3-hydroxy-2-methylpropionaldehyde.

DETAILED DESCRIPTION OF THE INVENTION

The process of the invention comprises hydroformylating allyl alcohol in the presence of a solvent and a catalyst. The catalyst of the invention comprises a rhodium complex and one or more phosphine ligands. The phosphine is a 6-bis(3,5-dialkylphenyl)phosphino-N-pivaloyl-2-aminopyridine or a 3-bis(3,5-dialkylphenyl)phosphino-2H-isoquinolin-1-one.

Preferred 6-bis(3,5-dialkylphenyl)phosphino-N-pivaloyl-2-aminopyridines have the formula:

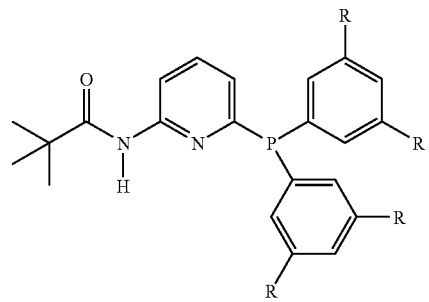

wherein each R is independently an n-alkyl group. Preferably, R is methyl, ethyl, or propyl. Any of the pyridine ring carbons may be substituted or unsubstituted.

The 6-bis(3,5-dialkylphenyl)phosphino-N-pivaloyl-2-aminopyridine ligand is most preferably 6-bis(3,5-dimethylphenyl)phosphino-N-pivaloyl-2-aminopyridine or 6-bis(3,5-diethylphenyl)phosphino-N-pivaloyl-2-aminopyridine.

Preferred 3-bis(3,5-dialkylphenyl)phosphino-2H-isoquinolin-1-ones have the formula:

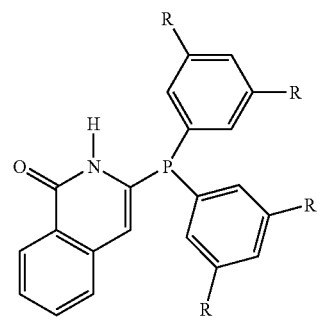

wherein each R is independently an n-alkyl group. Preferably, R is methyl, ethyl, or propyl. Any of the isoquinolone ring carbons may be substituted or unsubstituted.

The 3-bis(3,5-dialkylphenyl)phosphino-2H-isoquinolin-1-one is most preferably 3-bis(3,5-dimethylphenyl)phosphino-2H-isoquinolin-1-one or 3-bis(3,5-diethylphenyl)phosphino-2H-isoquinolin-1-one.

The 6-bis(3,5-dialkylphenyl)phosphino-N-pivaloyl-2-aminopyridine may be prepared by any possible method. For instance, 6-bis(3,5-dialkylphenyl)phosphino-N-pivaloyl-2-aminopyridines may be prepared by first reacting from 2-bromo-6-N-trifluoroacetylaminopyridine and n-butyl-lithium, followed by reaction with a chloro-bis(3,5-dialkylphenyl)phosphine, and then with potassium carbonate to form a 6-bis(3,5-dialkylphenyl)phosphino-2-aminopyridine, which is then reacted with pivaloyl chloride to produce the 6-bis(3,5-dialkylphenyl)phosphino-N-pivaloyl-2-aminopyridine. 3-Bis(3,5-dialkylphenyl)phosphino-2H-isoquinolin-1-ones may be prepared by first reacting potassium tert-butoxide and 1,3-dichloroisoquinoline to produce 1-tert-butoxy-3-bis(3,5-dimethylphenyl)phosphino isoquinoline, which is then reacted with n-butyl lithium, followed by the addition of chloro-bis(3,5-dialkylphenyl)phosphine to form 1-tert-butoxy-3-bis(3,5-dialkylphenyl)phosphino isoquinoline, which is then reacted with formic acid to produce the 3-bis(3,5-dialkylphenyl)phosphino-2H-isoquinolin-1-one.

The catalyst of the invention preferably comprises a rhodium complex and a mixture of the 6-bis(3,5-dialkylphenyl)phosphino-N-pivaloyl-2-aminopyridine and a 3-diarylphosphino-2H-isoquinolin-1-one. Alternatively, the catalyst of the invention preferably comprises a rhodium complex and a mixture of the 3-bis(3,5-dialkylphenyl)phosphino-2H-isoquinolin-1-one and a 6-diarylphosphino-N-pivaloyl-2-aminopyridine.

The catalyst of the invention also comprises a rhodium complex. Suitable rhodium complexes contain rhodium attached to ligand groups. The rhodium complex is preferably soluble in the solvent. There are no particular restrictions regarding the choice of ligands attached to the rhodium complex. For example, suitable ligands include hydrides, carbonyl, substituted and unsubstituted cyclopentadienyls, 2,4-alkanedionates, trialkyl phosphines, triaryl phosphines, diphosphines, and mixtures thereof. Particularly preferred ligands include carbonyl, acetylacetonate (2,4-pentanedionate), triphenylphosphine, and mixtures thereof. Examples of preferred rhodium complexes include (acetylacetonato)dicarbonylrhodium and tris(triphenylphosphine)rhodium carbonyl hydride.

The rhodium complex can be pre-associated with the 6-bis(3,5-dialkylphenyl)phosphino-N-pivaloyl-2-aminopyridine or 3-bis(3,5-dialkylphenyl)phosphino-2H-isoquinolin-1-one ligand prior to use in the hydroformylation reaction such that the 6-bis(3,5-dialkylphenyl)phosphino-N-pivaloyl-2-aminopyridine or 3-bis(3,5-dialkylphenyl)phosphino-2H-isoquinolin-1-one forms part of the rhodium complex, or it can be added separately. However, it is preferable to add the rhodium complex separate from the 6-bis(3,5-dialkylphenyl)phosphino-N-pivaloyl-2-aminopyridine or 3-bis(3,5-dialkylphenyl)phosphino-2H-isoquinolin-1-one. The molar ratio of the 6-bis(3,5-dialkylphenyl)phosphino-N-pivaloyl-2-aminopyridine or 3-bis(3,5-dialkylphenyl)phosphino-2H-isoquinolin-1-one ligand:rhodium complex is preferably in the range of 0.5:1 to 5:1.

Although not necessary, the catalyst may additionally comprise a trialkyl or triarylphosphine compound. The trialkyl or triarylphosphine compound is in addition to any phosphine ligand that may be associated with the rhodium complex. The trialkyl or triarylphosphine compound is a trisubstituted phosphine that is represented by the formula:

$(R^1)_3P$ wherein $R^1$ is an aryl or alkyl group. Suitable aliphatic $R^1$ groups include methyl, ethyl, n-butyl, sec-butyl, octyl, and decyl. Suitable aromatic $R^1$ groups include phenyl, tolyl, and naphthyl. The $R^1$ groups may be the same or are different, but preferably are the same. Preferably, the trialkyl or triarylphosphine is a triaryl phosphine. More preferably, the triaryl phosphine is triphenylphosphine or tritolylphosphine. Triphenyl phosphine is particularly preferred.

A reaction solvent is also required for the process of the invention. Typical solvents are those that are capable of solubilizing the rhodium complex and are not reactive to the hydroxyaldehydes that are produced in the hydroformylation step. Suitable solvents include any organic solvent having very low or minimal solubility in water. Preferred solvents include $C_5$-$C_{20}$ aliphatic hydrocarbons, $C_6$-$C_{20}$ aromatic hydrocarbons, alcohols, ethers, and mixtures thereof. Particularly preferred solvents include toluene, cyclohexane, methyl t-butyl ether, isopropanol, and mixtures thereof.

Typical reaction conditions for the hydroformylation step are mild to favor the formation of the linear 4-hydroxybutyraldehyde (HBA) rather than branched 3-hydroxy-2-methylpropionaldehyde (HMPA) reaction product. Reaction conditions are preferably in the range of from 20 to 120° C. and pressures of from 20 to 1000 psig, more preferably from 45 to 110° C. and 30 to 800 psig, and most preferably from 50 to 100° C. and 40 to 600 psig. The molar ratio of $CO:H_2$ is typically about 1:1, although the ratio can vary considerably. The partial pressure of CO is typically within the range of 5 to 300 psig. The partial pressure of hydrogen is typically within the range of 40 to 300 psig. The reaction is conducted at these conditions until a predominance of the allyl alcohol has reacted, e.g. 60 to 99.9%, the products being largely 4-hydroxybutyraldehyde with some branched reaction products. The amount of reaction time is not critical, but usually a reaction time of 0.5 to 4 hours is adequate.

Preferably, the allyl alcohol starting concentration on a reaction solvent to feed basis is in the range of 5 to 40 percent by weight in the solvent; more preferably, lower concentration in the range of 5 to 10 percent by weight may be used.

Preferably, the hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference. Preferably, the liquid phase hydrogen:carbon monoxide molar ratio is in the range of from 10:1 to 1:2, more preferably from 5:1 to 1:2.

Following the hydroformylation step, the HBA product is preferably separated from the solvent and catalyst by water extraction in an extraction vessel. Water extraction methods are well known in the art and can be affected by any suitable means, such as mixer-settlers, packed or trayed extraction columns, rotating disk contactors, or passed to a settling tank for resolution of the mixture into aqueous and organic phases. HBA, and any HMPA, remains soluble in the water (aqueous) phase and is separated from the solvent (organic) phase.

The 4-hydroxybutyraldehyde (and any 3-hydroxy-2-methylpropionaldehyde) reaction product is preferably subjected to an additional step of hydrogenating the 4-hydroxybutyraldehyde in the presence of a hydrogenation catalyst to produce 1,4-butanediol (BDO). Hydrogen is added to the reaction vessel for the hydrogenation. Suitable hydrogenation catalysts include any Group VIII metal, such as nickel, cobalt, ruthenium, platinum, and palladium, as well as copper, zinc and chromium and mixtures and alloys thereof. Especially preferred are nickel catalysts. Most preferred are Raney® nickel-type and fixed bed nickel catalysts.

The hydrogenation reaction conditions are preferably in the range of from 60 to 200° C. and pressures of from 200 to 1000 psig, more preferably from 80 to 140° C. and 300 to 1000 psig. Generally reaction times of 1 to 10 hours are appropriate. The hydrogenation reaction converts HBA to BDO and HMPA to MPD, along with a small amount of other co-product/byproducts. The linear:branched (BDO:MPD) product ratio is approximately that of the HBA:HMPA feed to hydrogenation.

The following examples merely illustrate the invention. Those skilled in the art will recognize many variations that are within the spirit of the invention and scope of the claims.

EXAMPLE 1

Preparation of Aminopyridine Phosphines 1A, 1B, 1C, and 1D: Phosphine 1A is prepared according to the procedure described below. Phosphines 1B, 1C, and 1D are prepared using analogous procedures employing the suitable chlorophosphines.

Phosphine 1A: 6-bis(3,5-dimethylphenyl)phosphino-N-pivaloyl-2-aminopyridine.

Comparative Phosphine 1B: 6-diphenylphosphino-N-pivaloyl-2-aminopyridine.

Comparative Phosphine 1C: 6-dicyclohexylphosphino-N-pivaloyl-2-aminopyridine.

Comparative Phosphine 1D: 6-diethylphosphino-N-pivaloyl-2-aminopyridine.

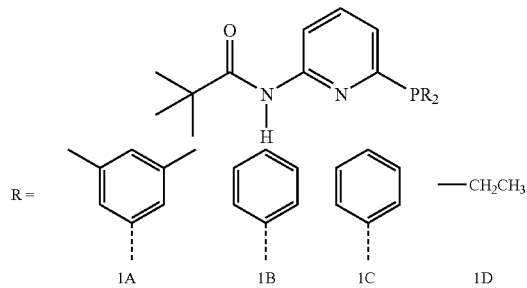

A solution of n-butyl lithium in hexanes (1.6 M, 2.9 mL, 4.6 mmol) is added to a solution of 6-bromo-2-N-trifluoroacetylaminopyridine (0.62 g, 2.3 mmol) in tetrahydrofuran (15 mL) at −100° C. After stirring at constant temperature for 90 minutes, a solution of bis(3,5-dimethylphenyl)chlorophosphine (501 μL, 2.5 mmol) in tetrahydrofuran (4 mL) is introduced drop-wise and stirred for 90 minutes at −100° C. The solution is then warmed to 35° C. and stirred for 12 hours prior to water (50 μL 2.80 mmol) addition. The solvents are removed under reduced pressure, dichloromethane (9 mL) is added to the residue, and the resulting suspension is filtered through silica pad and concentrated. A suspension of potassium carbonate (3.2 g, 21.9 mmol) in methanol (20 mL) is added and then stirred at 60° C. for 4 hours followed by addition of a saturated sodium bicarbonate solution (14 mL). The aqueous phase is then extracted with ethyl acetate (3×25 mL) and the combined extracts are percolated through a column of magnesium sulfate-ZSM-5. The filtrate is concentrated under reduced pressure and the off-white solid purified by flash chromatography yielding 6-bis(3,5-dimethylphenyl) phosphino-2-aminopyridine (0.65 g, 84%).

To a solution of 6-bis(3,5-dimethylphenyl)phosphino-2-aminopyridine (0.19 g, 0.58 mmol) in dichloromethane (45 mL) at 0° C., triethylamine (152 μL, 1.1 mmol) and pivaloyl chloride (107 μL, 0.87 mmol) are added consecutively. The solution is slowly warmed to ambient temperature, stirred for 40 hours, and concentrated under reduced pressure. The remaining suspension is stirred with activated charcoal (0.25 g) and filtered through a Celite pad. The filtrate is concentrated under reduced pressure and the white residue is purified by column chromatography to yield 6-bis(3,5-dimethylphenyl)phosphino-N-pivaloyl-2-aminopyridine (0.16 g, 65%).

EXAMPLE 2

Preparation of Isoquinolone Phosphines 2A, 2B, 2C and 2D: Phosphine 2A is prepared according to the procedure described below. Phosphines 2B, 2C, and 2D are prepared using analogous procedures employing the suitable triphosphines.

Phosphine 2A: 3-bis(3,5-dimethylphenyl)phosphino-2H-isoquinolin-1-one.

Comparative Phosphine 2B: 3-diphenylphosphino-2H-isoquinolin-1-one.

Comparative Phosphine 2C: 3-dicyclohexylphosphino-2H-isoquinolin-1-one.

Comparative Phosphine 2D: 3-diethylphosphino-2H-isoquinolin-1-one.

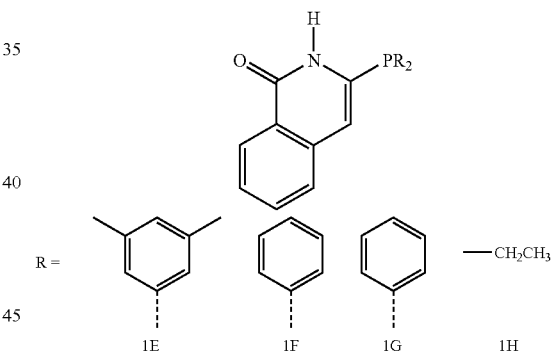

Potassium tert-butoxide (2.2 g, 19.3 mmol) is added to a solution of 1,3-dichloroisoquinoline (3.2 g, 16.12 mmol) in toluene (40 mL). The solution is then heated at reflux, cooled to ambient temperature, and filtered through a silica pad. The filtrate is concentrated under reduced pressure and the residual yellow liquid is purified by distillation (210° C., 0.1 mm Hg), yielding 1-tert-butoxy-3-chloroisoquinoline (3.4 g, 89%).

At −78° C., sodium (0.28 g, 12.3 mmol) is added slowly to liquid ammonia (40 mL) followed by tris(3,5-dimethylphenyl)phosphine (2.1 g, 6.0 mmol), and the resulting mixture is stirred for 2 hours. A solution of 1-tert-butoxy-3-chloroisoquinoline (1.4 g, 6.0 mmol) in tetrahydrofuran (6 mL) is then added drop-wise and the resulting mixture slowly warmed to ambient temperature over 16 hours. The residue is quenched with water (30 mL), extracted with diethyl ether (3×25 mL), and the combined extracts are percolated through a column of magnesium sulfate-ZSM-5. The filtrate is concentrated under reduced pressure and the opaque residue is purified by a re-crystallization from methanol, yielding 1-tert-butoxy-3-(bis(3,5-dimethylphenyl)phosphino)isoquinoline (0.94 g, 73%) as a white solid.

1-tert-butoxy-3-(bis(3,5-dimethylphenyl)phosphino)isoquinoline (0.96, 2.2 mmol) is dissolved in neat concentrated formic acid (9 mL), and the solution is stirred at ambient temperature for 1 hour. Precipitation of the isoquinolone was induced by dilution with $H_2O$ (25 mL), and the suspension is filtered through a glass frit. The white flakes are washed with 70% formic acid solution (3×5 mL). The combined aqueous formic acid filtrates are concentrated under reduced pressure, and the opaque residue is crystallized from acetone yielding 3-bis(3,5-dimethylphenyl)phosphino-2H-isoquinolin-1-one (0.55 g, 66%).

EXAMPLE 3

Hydroformylation Reaction Using Phosphines

Allyl alcohol is hydroformylated using phosphines 1A-1D and 2A-2D according to the following procedure:

A solution of phosphine (0.12 mmol) in dry degassed isopropanol solvent (4 mL) is added under a stream of argon or nitrogen to [Rh(CO)$_2$(acac)] (0.04 mmol) under an argon atmosphere. The resulting solution is transferred in a gastight syringe to a 25-mL autoclave under an argon atmosphere. The autoclave is flushed twice with a 1:1 CO/H$_2$ mixture and then pressurized to 30 bar with the CO/H$_2$ mixture. The autoclave is then heated to 90° C. with stirring, the pressure is increased to 39 bars, allyl alcohol (1 mL) is then injected from a side-arm, and the autoclave pressurized to 40 bar with the CO/H$_2$ mixture. The autoclave is kept at a constant pressure of 40 bar, and the gas uptake of the reaction is monitored in a ballast vessel from which the gas is delivered. When there is no further gas uptake, the autoclave is cooled and depressurized. The resulting solution is analyzed by gas chromatography to determine the products of the reaction.

The reaction produces HBA, HMPA, and C$_3$ products (n-propanol and propionaldehyde). Some of the reactions produce BDO and MPD, as well, showing that some reactions undergo hydrogenation under the present conditions in addition to the hydroformylation. In some cases when BDO if formed 1-butanol is also formed via BDO dehydration. In these cases 1-butanol is also defined as a linear alcohol product.

The aldehyde selectivity (i.e., moles HBA+HMPA produced/moles allyl alcohol converted*100%) and the aldehyde L:B ratio (linear:branched; HBA:HMPA) is measured. For those reactions that also produce BDO, 1-butanol and MPD, the alcohol selectivity (i.e., moles BDO+1-butanol+MPD produced/moles allyl alcohol converted*100%) and the ratio of alcohol L:B (linear:branched) is also measured. The total selectivity (HBA, HMPA, BDO, 1-butanol, MPD) demonstrates the is effectiveness of the catalyst systems at hydroformylation. The results are shown in Table 1.

EXAMPLE 4

Hydroformylation Reaction Using Phosphine Mixtures

Allyl alcohol is hydroformylated according to the procedure of Example 3, with the exception that a mixture of 2 different phosphines (0.06 mmol each) is used. Table 2 shows the results and the phosphines used in the mixtures.

TABLE 1

Phosphine Comparisons

| Phosphine | Aldehyde Selectivity | Aldehyde L:B ratio | Alcohol Selectivity | Alcohol L:B ratio | Total Selectivity |
|---|---|---|---|---|---|
| 1A | 96 | 16.5 | — | — | 96 |
| 1B* | 83 | 3.4 | 2 | 1 | 85 |
| 1C* | 9 | 2.5 | 71 | 2.7 | 80 |
| 1D* | 59 | 1.5 | 5 | 0.2 | 64 |
| 2A | 95 | 16.8 | — | — | 95 |
| 2B* | 86 | 3.6 | 1 | 1 | 87 |
| 2C* | 10 | 2.9 | 73 | 3.0 | 83 |
| 2D* | 66 | 1.7 | 5 | 0.4 | 69 |

*Comparative Example

TABLE 2

Comparison of Phosphine Mixtures

| Phosphine Mixtures | Aldehyde Selectivity | Aldehyde L:B ratio | Alcohol Selectivity | Alcohol L:B ratio | Total Selectivity |
|---|---|---|---|---|---|
| 1A-2A | 99 | 23.1 | — | — | 99 |
| 1A-2B | 97 | 19.1 | — | — | 97 |
| 1A-2C | 60 | 16.0 | 38 | 16.1 | 98 |
| 1A-2D | 35 | 18.7 | 61 | 19.0 | 96 |
| 2A-1B | 96 | 18.7 | — | — | 96 |
| 2A-1C | 62 | 16.2 | 35 | 16.3 | 97 |
| 2A-1D | 33 | 18.8 | 63 | 19.1 | 96 |
| 1B-2B* | 95 | 11.1 | — | — | 95 |
| 1B-2C* | 57 | 10.2 | 36 | 10.6 | 93 |
| 1B-2D* | 30 | 11.4 | 63 | 11.5 | 93 |
| 1C-2B* | 61 | 9.9 | 34 | 9.9 | 95 |
| 1C-2C* | 36 | 6.4 | 57 | 5.1 | 93 |
| 1C-2D* | 13 | 9.5 | 80 | 9.8 | 93 |
| 1D-2B* | 35 | 11.4 | 64 | 11.7 | 99 |
| 1D-2C* | 14 | 9.2 | 79 | 9.7 | 93 |
| 1D-2D* | 72 | 1.7 | 4 | 0.3 | 76 |

*Comparative Example

We claim:

1. A process to produce 4-hydroxybutyraldehyde comprising reacting allyl alcohol with carbon monoxide and hydrogen in the presence of a solvent and a catalyst comprising a rhodium complex and a phosphine selected from the group consisting of a 6-bis(3,5-dialkylphenyl)phosphino-N-pivaloyl-2-aminopyridine and a 3-bis(3,5-dialkylphenyl)phosphino-2H-isoquinolin-1-one.

2. The process of claim 1 wherein the phosphine is 6-bis(3,5-dimethylphenyl)phosphino-N-pivaloyl-2-aminopyridine.

3. The process of claim 1 wherein the phosphine is 3-bis(3,5-dimethylphenyl)phosphino-2H-isoquinolin-1-one.

4. The process of claim 1 wherein the phosphine is a mixture of the 6-bis(3,5-dialkylphenyl)phosphino-N-pivaloyl-2-aminopyridine and a 3-diarylphosphino-2H-isoquinolin-1-one.

5. The process of claim 1 wherein the phosphine is a mixture of the 3-bis(3,5-dialkylphenyl)phosphino-2H-isoquinolin-1-one and a 6-diarylphosphino-N-pivaloyl-2-aminopyridine.

6. The process of claim 1 wherein the solvent is selected from the group consisting of $C_5$-$C_{20}$ aliphatic hydrocarbons, $C_6$-$C_{12}$ aromatic hydrocarbons, ethers, alcohols, and mixtures thereof.

7. The process of claim 1 wherein the solvent is selected from the group consisting of toluene, cyclohexane, methyl t-butyl ether, isopropanol, and mixtures thereof.

8. The process of claim 1 wherein the rhodium complex comprises rhodium and ligands selected from the group consisting of hydride, carbonyl, trialkyl phosphines, triaryl phosphines, diphosphines, cyclopentadienyls, 2,4-alkanedionates, and mixtures thereof.

9. The process of claim 1 further comprising hydrogenating the 4-hydroxybutyraldehyde in the presence of a hydrogenation catalyst to form 1,4-butanediol.

10. A catalyst comprising a rhodium complex and a phosphine selected from the group consisting of a 6-bis(3,5-dialkylphenyl)phosphino-N-pivaloyl-2-aminopyridine and a 3-bis(3,5-dialkylphenyl)phosphino-2H-isoquinolin-1-one.

11. The catalyst of claim 10 which comprises the rhodium complex and 6-bis(3,5-dimethylphenyl)phosphino-N-pivaloyl-2-aminopyridine.

12. The catalyst of claim 10 which comprises the rhodium complex and 3-bis(3,5-dimethylphenyl)phosphino-2H-isoquinolin-1-one.

13. The catalyst of claim 10 which comprises the rhodium complex and a mixture of the 6-bis(3,5-dialkylphenyl)phosphino-N-pivaloyl-2-aminopyridine and a 3-diarylphosphino-2H-isoquinolin-1-one.

14. The catalyst of claim 10 which comprises the rhodium complex and a mixture of the 3-bis(3,5-dialkylphenyl)phosphino-2H-isoquinolin-1-one and a 6-diarylphosphino-N-pivaloyl-2-aminopyridine.

\* \* \* \* \*